United States Patent

Cartmell et al.

[11] Patent Number: 5,899,871
[45] Date of Patent: May 4, 1999

[54] WOUND PACKING

[75] Inventors: James Vernon Cartmell, Xenia; Wayne R. Sturtevant, Centerville; Michael Lee Wolf, West Milton, all of Ohio

[73] Assignee: NDM, Inc., Utica, N.Y.

[21] Appl. No.: 08/456,166

[22] Filed: May 31, 1995

Related U.S. Application Data

[60] Division of application No. 08/144,003, Nov. 1, 1993, Pat. No. 5,695,456, which is a continuation-in-part of application No. 07/862,456, Apr. 2, 1992, Pat. No. 5,429,589.

[51] Int. Cl.$^6$ .................................................. A61F 13/00
[52] U.S. Cl. ............................ 602/43; 602/53; 602/75; 602/48; 604/304
[58] Field of Search .................... 602/41, 42, 43, 602/46, 48, 49, 53, 58, 59, 60, 75; 604/11, 13, 304, 309, 368, 964

[56] References Cited

U.S. PATENT DOCUMENTS

| | | |
|---|---|---|
| 1,562,656 | 11/1925 | Park . |
| 2,772,999 | 12/1956 | Masci et al. . |
| 2,858,830 | 11/1958 | Robins . |
| 3,419,345 | 12/1968 | Parrish . |
| 3,993,553 | 11/1976 | Assarsson et al. . |
| 3,998,215 | 12/1976 | Anderson et al. . |
| 4,146,027 | 3/1979 | Hoey ........................................... 602/46 |
| 4,171,047 | 10/1979 | Doyle et al. . |
| 4,246,139 | 1/1981 | Witt . |
| 4,327,728 | 5/1982 | Elias . |
| 4,338,371 | 7/1982 | Dawn et al. . |
| 4,377,160 | 3/1983 | Romaine ................................... 602/75 |
| 4,389,211 | 6/1983 | Lenaghan . |
| 4,569,861 | 2/1986 | Smith et al. . |
| 4,685,909 | 8/1987 | Berg et al. . |
| 4,717,378 | 1/1988 | Perrault et al. . |
| 4,787,885 | 11/1988 | Binder . |
| 4,838,885 | 6/1989 | Bernardin . |
| 4,842,593 | 6/1989 | Jordan et al. . |
| 4,842,597 | 6/1989 | Brook . |
| 4,848,329 | 7/1989 | Dardik . |
| 4,865,596 | 9/1989 | Weisman et al. . |
| 4,909,244 | 3/1990 | Quarfoot et al. . |
| 4,930,500 | 6/1990 | Morgan . |
| 4,983,773 | 1/1991 | Patience et al. . |
| 4,984,570 | 1/1991 | Langen et al. . |
| 5,059,424 | 10/1991 | Cartmell et al. . |
| 5,061,259 | 10/1991 | Goldman et al. . |
| 5,087,242 | 2/1992 | Petelenz et al. . |
| 5,112,618 | 5/1992 | Cartmell et al. . |
| 5,115,801 | 5/1992 | Cartmell et al. . |
| 5,135,472 | 8/1992 | Hermann et al. . |
| 5,340,363 | 8/1994 | Fabu ........................................... 602/48 |
| 5,395,305 | 3/1995 | Koide et al. .............................. 602/48 |

FOREIGN PATENT DOCUMENTS

| | | |
|---|---|---|
| 659528 | 3/1963 | Canada . |
| 363930 | 12/1931 | United Kingdom . |
| 2249266 | 5/1992 | United Kingdom . |

*Primary Examiner*—Corrine M. McDermott
*Assistant Examiner*—Cris L. Rodriguez
*Attorney, Agent, or Firm*—Killworth, Gottman, Hagan & Schaeff, LLP

[57] ABSTRACT

A sterile wound packing material and package therefor is provided, which wound packing is flexible and conformable to deep and/or irregular shaped wounds, is compact and easily dispensed, and which can be stored indefinitely. The wound packing may also be used for absorbing wound exudate and immediately discarded or may be designed to remain in place for extended periods during healing. The wound packing includes a sterile, wound packing of a flexible material capable of absorbing wound exudate, with the flexible material being in the form of a substantially flat, coiled, spirally-cut layer and a package therefor. In certain embodiments of the invention where it is desired that the wound packing remain in place for an extended period, the flexible material is impregnated with a hydrogel, which may be a "wet" hydrogel (i.e., one containing substantial amounts of water) or a dehydrated hydrogel which is substantially devoid of water but becomes hydrated in use.

6 Claims, 6 Drawing Sheets

WOUND PACKING

CROSS REFERENCE TO RELATED APPLICATIONS

This application is a division of U.S. application Ser. No. 08/144,003, filed Nov. 1, 1993, now U.S. Pat. No. 5,695,456 which is a continuation-in-part of U.S. application Ser. No. 07/862,456, filed Apr. 2, 1992, now U.S. Pat. No. 5,429,589 and entitled HYDROGEL GAUZE WOUND DRESSING. This application is also related to U.S. application Ser. No. 07/921,916, filed Jul. 29, 1992, and entitled HYDROGEL GAUZE, now abandoned, and U.S. application Ser. No. 08/082,806, filed Jun. 25, 1993, and entitled HYDROGEL GAUZE.

BACKGROUND OF THE INVENTION

The present invention relates to a sterile wound packing and a package therefor, and, more particularly to a wound packing in the form of a flexible spirally-cut layer capable of absorbing wound exudate and a package for dispensing the wound packing.

Secreting skin wounds, such as decubitus ulcers and open surgical wounds, have long presented a medical challenge in keeping such wounds sterile and relatively dry. Deep wounds provide an even greater challenge. The accumulation of wound exudate, such as blood, pustulation, and other wound fluids, in wound crevices, promotes growth of bacteria and other organisms which cause infection and delay the healing process. Such wound exudate may also cause maceration of tissue adjacent the wound and support infection thereof.

However, since it is often desirable to allow a wound to heal in a slightly "moist" state, which is believed to accelerate healing, excess wound exudate must be removed. If excess wound exudate remains in or on a wound, a "blister" of exudate can form under the wound dressing which is not only unsightly, but also may cause the dressing to leak, thereby defeating the aim of sterility. However, existing methods of aspiration can lead to wound infection or can destroy sterility. Additionally, it is not desirable to remove all exudate as that would result in a "dry" wound resulting in a slower healing process.

There is a substantial body of prior art relating to wound and/or surgical dressings or packings for treating skin lesions, such as decubitus ulcers and open wounds. In some instances, the wound dressing or packing may be designed to be only temporary, such as the use of gauze to absorb blood and/or other wound exudate. In others, the wound dressing is designed to be more permanent in nature, remaining in place for several hours or days during the healing process. In yet other instances, the wound dressing material is designed to be biodegradable and to break down over an extended period of time as a wound heals.

Aqueous moisture absorbing materials, such as a hydrogel material with a polyethylene glycol liquid curing agent, as disclosed in Spence, U.S. Pat. No. 4,226,232, have been used as dressings on a wound site, but cannot be sterilized by irradiation due to the formation of free radicals within the aqueous material. Another aqueous absorbing material used to absorb wound exudate is a hydrophilic polymer as disclosed in Rawlings et al, U.S. Pat. No. 4,657,006. Rawlings et al disclose a wound dressing which comprises a hydrophilic polymer having moisture and vapor permeability characteristics. However, a problem with the Rawlings et al wound dressing is that the wound exudate absorbed by the hydrophilic polymer hardens or solidifies the polymer, allowing pockets to develop between the polymer and the wound, thereby providing an excellent environment for bacteria proliferation.

In addition, wound dressings used in the past have not been conducive for healing extremely deep wounds and wounds having irregular shapes. To that end, wound dressings and surgical sponges formed from gauze and foam materials have been used for many years in surgical practice. These sponges and wound dressings have attempted to retain both the advantages of thin, soft and flexible single layer dressings and the absorptive cushioning and insulating properties of thicker pad-like structures. As a result, the sponges and wound dressings have traditionally been formed of multiple layers of thin, soft, low-count gauze material which are unified along fairly widely separated lines usually extending longitudinally or transversely.

Although such wound dressings and surgical sponges have been found useful in the past, none have provided the capability of absorbing large amounts of wound exudate without inhibiting the healing of the wound to which they are contacted. Most all of these dressings, including gauze and sponges, adhere to the wound upon removal, thereby damaging the wounds to which they are attached. This in turn prolongs the healing of such wounds. It would therefore be desirable to have a wound dressing or packing having a structure which is thin, flexible and soft yet absorbs wound exudate in the same manner as the more thick pad-like wound dressings.

Another problem with prior wound dressings or packings is the need to maintain their sterile condition both prior to use and during application to a wound. To maintain sterility, the wound dressings are packaged in metal foil or metallized plastic containers. Dry gauze dressings are often packaged in small glass bottles, while aqueous hydrogel wound dressings require moisture barrier packaging to prevent them from drying out during storage prior to use. In many instances, the packaging and labor requirements for such products represent a significant additional cost over and above the cost of the wound dressing itself and/or is difficult for an end user to open or dispense the wound dressing.

Accordingly, there is a need in the art for a wound packing which is especially conducive for wounds which penetrate the surface of the skin. There is also a need for such a wound packing which has a thin, flexible and soft structure so as to permit the wound packing to be sterilized and readily available for application to a draining wound having irregular shapes and depths. Finally, there is a need for such a wound dressing which can be conveniently packaged and dispensed while maintaining its sterility.

SUMMARY OF THE INVENTION

The present invention meets those needs by providing a sterile wound packing material and package therefor which wound packing is flexible and conformable to deep and/or irregular shaped wounds, is compact and easily dispensed, and which can be stored up to several years. The wound packing of the present invention may also be designed to be used for absorbing wound exudate and immediately discarded or may be designed to remain in place for extended periods during healing.

According to one aspect of the present invention, a sterile wound packing is provided and includes a sterile, wound packing and a package therefor. The wound packing includes a flexible material capable of absorbing wound exudate, with the flexible material being in the form of a substantially flat, coiled, spirally-cut layer. The flexible material is selected from the group consisting of woven gauze, fabric, nonwoven natural or synthetic fibers, polymeric sheets and films, and the like. In certain embodiments of the invention where it is desired that the wound packing remain in place for an extended period, the flexible material is impregnated with a hydrogel, which may be a "wet" hydrogel (i.e., one containing substantial amounts of water) or a dehydrated hydrogel which is substantially devoid of water but becomes hydrated in use. Alternatively, the flexible material may be impregnated with a hydrocolloid comprising particulate hydrophilic polymers.

The package for the packing material includes sealed first and second sheets with the flexible wound packing material therebetween. The first and second sheets of the package are made of any suitable material capable of maintaining the sterility of the contents of the package such as metal foil, metal-coated polymer, polymer, paper, coated paper, Tyvek® film, or any non-metallized plastic film. The package may be designed to be opened by puncturing one of the sheets to form an opening in the package. The spirally-cut packing may then be removed by pulling on one end thereof out through the opening. The wound packing may be cut to length as needed or may be designed to be packaged in different widths and lengths.

To aid in opening the package, the package may include means for stiffening the package to promote easy puncture. The stiffening means comprise card stock or a stiff polymeric sheet disposed in the package. Alternatively, the stiffening means comprise a release liner on the flexible material. In another alternative embodiment, one or both of the sheets forming the package may include a weakened area, again to aid in opening the package. The weakened area may comprise, for example, a pattern of score lines or perforations which can be readily broken to facilitate access to an end of the spirally-cut wound packing in the package. However, in order to maintain sterility of the package, the score lines or perforations should not penetrate the package.

In another embodiment, the package includes an opening in one of the first and second sheets located adjacent one end of the packing material for providing access to the packing material, and removable means for sealing the opening. Again, to aid in the opening of the package, there may be means for stiffening the area around the opening such as card stock laminated to an inner surface of the package around the opening. The opening may be located substantially at the center of the package adjacent one end of the spirally-cut wound packing or, alternatively, near an edge of the package adjacent the opposite end of the wound packing.

In an alternative embodiment, the entire wound packing may be removed from the package by peeling apart the first and second sheets at a designated portion of the package where a free-lifting edge or corner is provided.

Accordingly, it is a feature of the present invention to provide a wound packing which is flexible and conformable to deep and/or irregular shaped wounds, is compact and easily dispensed, and which can be stored for several years in a sterile condition. It is another feature of the present invention that the wound packing may also be designed to be used for absorbing wound exudate and then immediately discarded or may be designed to remain in place for extended periods during healing. These, and other features and advantages of the present invention will become apparent from the following detailed description, the accompanying drawings, and the appended claims.

DETAILED DESCRIPTION OF THE PREFERRED EMBODIMENTS

Figure 1:
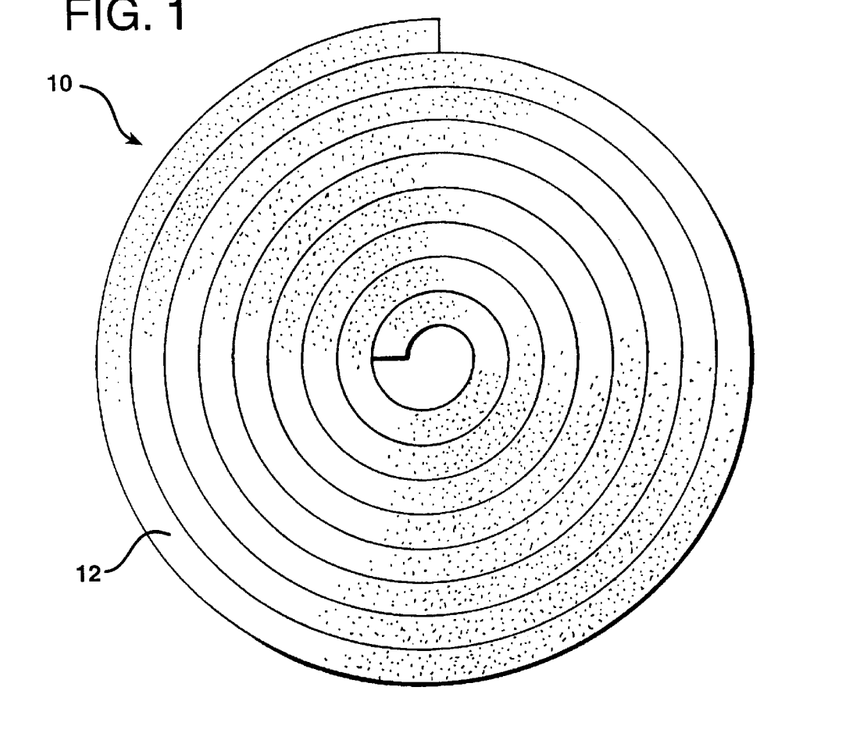
FIG. 1 is a top view of the wound packing illustrating the spiral-cut configuration.

The present invention provides a sterile wound packing 10 in the form of a thin, flexible structure suitable for use in the treatment of wounds on a patient. As shown in FIG. 1, the wound packing 10 comprises a flexible absorbent layer 12 which may optionally have a dehydrated or hydrated hydrogel material impregnated therein for absorbing wound exudate. The flexible layer may alternatively be impregnated with a hydrocolloid material comprising discrete particles of hydrophilic polymers. Such hydrocolloid materials are described, for example, in EPO Patent Application No. 88306649 assigned to Fulmer Yarsley Limited and EPO Patent Application No. 86302696.9 assigned to The Proctor & Gamble Company, the disclosures of which are incorporated by reference. Other hydrocolloid materials which are known in this art may also be utilized. In addition to the hydrogel or hydrocolloid materials, if desired, a medicament may be impregnated in the flexible absorbent layer.

While those skilled in the art will appreciate the difficulty in illustrating the presence of a hydrogel material in absorbent layer 12, it should be understood that the optional hydrogel material when used is preferably completely impregnated in the interstices between fibers of the absorbent layer 12.

It is preferred that the absorbent layer 12 be formed of material which is capable of absorbing wound exudate and/or blood cells, as well as being capable of supporting the optional hydrogel material. Those skilled in the art will appreciate that materials having interstices within which materials may be absorbed or impregnated are particularly suitable for such purposes. Examples of suitable materials for absorbent layer 12 include woven gauze, natural or synthetic fabrics, nonwoven natural or synthetic fibers (e.g., felts), or polymeric sheets and films to the extent that they can be fabricated to include interstices and be absorbent. Absorbent layer 12 can comprise a single fibrous layer, a plurality of layers stacked one atop the other, or a felt-like nonwoven material. Typically, the material of absorbent layer 12 will have a thickness of from several mils to a few hundred mils.

Materials such as polyester scrim may also be used as wound packing if used in combination with the absorbing hydrogel material. However, if the wound packing is to be used for absorption of blood cells, the packing material should comprise an absorbent structure as hydrogels in general do not absorb blood cells.

As shown, wound packing 10 is in the form of a substantially flat, coiled spiral-cut layer of material. As explained in greater detail below, the material may be manufactured in the form of a continuous web which can then optionally be impregnated with a hydrogel and cut into desired sizes. For example, an approximately 5 inch diameter disk of absorbent material may be spiral cut into a continuous ¼ inch width strip to provide over six feet of wound packing. Similarly, an approximately 8 inch diameter disk of absorbent material may be spiral cut into a continuous 1 inch width strip to provide over three feet of wound packing. Those skilled in this art will recognize that there are many combinations of widths and lengths of the wound packing material which can be manufactured. Because of the spiral cut design, the wound packing may be easily packaged compactly and in a variety of widths and lengths.

Figure 2:
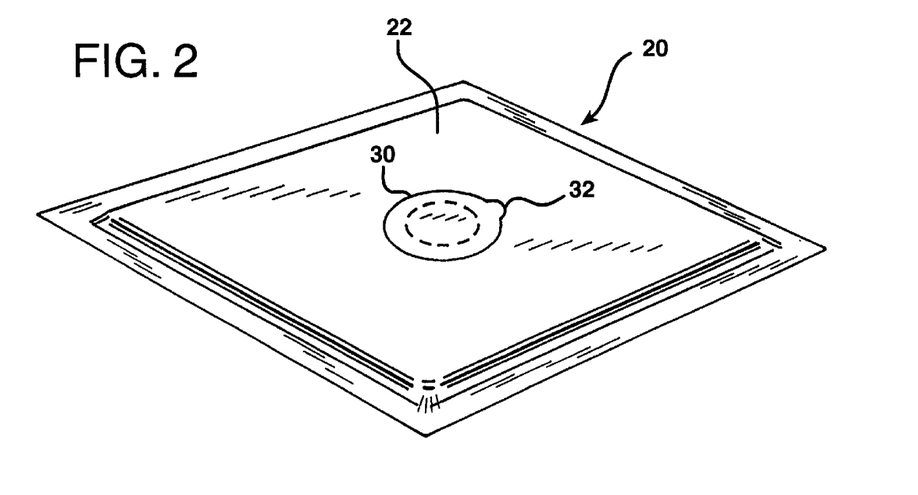
FIG. 2 is a perspective view of a sealed package containing the wound packing with a centrally located access hole sealed by a tab with a free-lifting edge.
Figure 3:
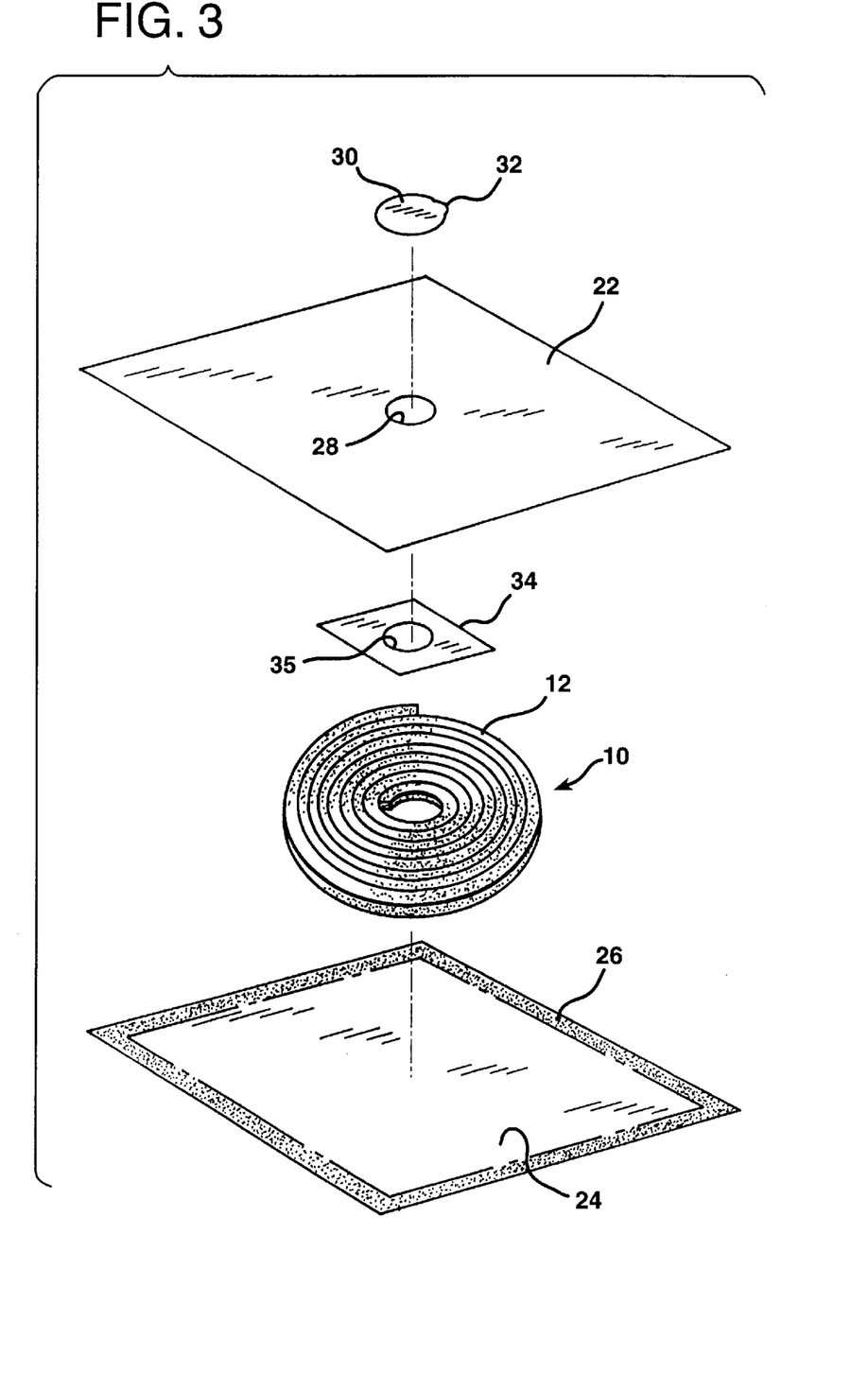
FIG. 3 is an exploded perspective view of the wound packing and package of FIG. 2, including a reinforcement or stiffener.

Referring now to FIGS. 2 and 3, a package 20 is provided for wound packing 10. Package 20 includes peripherally sealed first and second sheets 22, 24 with wound packing 10 therebetween. First and second sheets 22, 24 may be made from any suitable material capable of maintaining the sterility of the wound packing 10 within the package. Examples of suitable sheet material include metal foils, metal coated polymer sheets, polymers (including but not limited to those which provide moisture and/or gas barrier properties), paper, or coated paper. Where an optional hydrated hydrogel is impregnated into the wound packing, it is preferred that packaging with moisture barrier properties be used to insure a long shelf life for the package.

The sheets may be heat sealed together or adhesively sealed, such as by a bead of peripheral adhesive 26 on one or both sheets. Alternatively, any sealing process which results in an air-tight seal to maintain the sterility of the wound packing within the package is suitable. Package 22 may be designed to be opened by puncturing one or both of sheets 22, 24 to form an opening through which one end of absorbent layer 12 may be pulled.

In the embodiment shown in FIGS. 2 and 3, package 20 includes a precut opening 28 in sheet 22 which is located adjacent one end of the spirally-cut wound packing. In FIGS. 2 and 3, this opening is shown as being centrally located on the package over the end of the wound packing nearest the center of absorbent layer 12. Alternatively, the opening may be located over the opposite end of the wound packing. While being shown for illustration purposes as being circular, the size and shape of the opening is not critical so long as ready access to one end of wound packing 10 is provided.

Package 20 includes removable means for sealing the opening such as a tab 30 which may be adhered or otherwise sealed over opening 28. If a pressure sensitive adhesive is used to seal the tab over opening 28, then the tab may also be used to reseal the opening if desired after a desired length of wound packing 10 has been removed and cut. Tab 30 may include a free or clean-lifting edge 32 which may be grasped to facilitate its removal.

Figure 9:
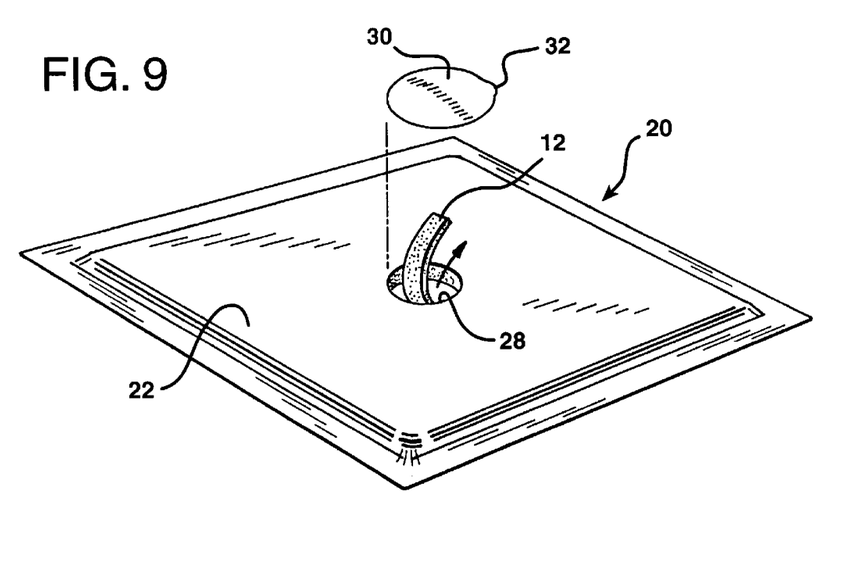
FIG. 9 is a perspective view of a package containing a spiral cut wound packing being removed through a centrally located access hole after removal of the sealing tab.

Referring now to FIG. 9, once tab 30 has been removed, an end of absorbent material 12 is shown being pulled in the direction of the arrow from opening 28 to a desired length or amount. The flexible material may then be cut. Alternatively, the entire contents of package 20 may be removed and used at the same time.

As shown in FIG. 3, package 20 may also include a stiffening means therein to promote easy puncture or opening of the package. Such stiffening means may comprise card stock 34 or a stiff polymeric sheet disposed in the package. Card stock 34 may itself include a corresponding opening 35 and be positioned or secured to the underside of sheet 22 beneath opening 28.

Figure 4:
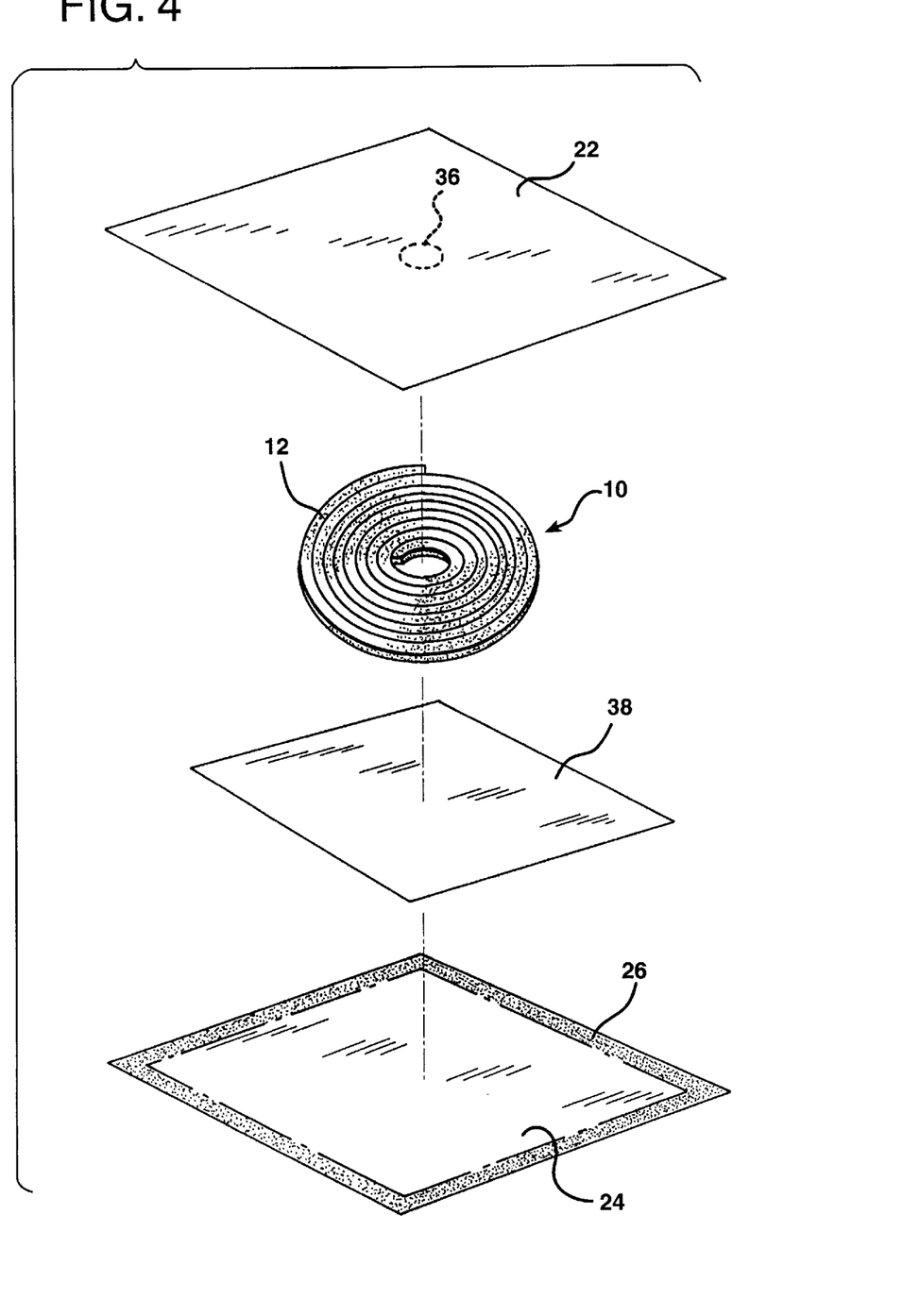
FIG. 4 is an exploded perspective view of an another embodiment of the wound packing and package.

In an alternative embodiment of the invention shown in FIG. 4, where like reference numerals represent like elements, sheet 22 includes a weakened area 36 to aid in the opening of package 20. Weakened area 36, as shown, comprises a series of score lines or perforations which can be readily broken to facilitate access to an end of absorbent layer 12. Again, the pattern and size of the weakened area is not critical as long as ready access to an end of wound packing 10 is provided. However, care should be taken so that the score lines or perforations do not penetrate completely into the package and cause the packing to lose its sterility. In the embodiment shown in FIG. 4, a release liner 38 underlies flexible absorbent layer 12. Release liner 38 may also act as the stiffening means to promote easy opening of package 22.

Figure 10:
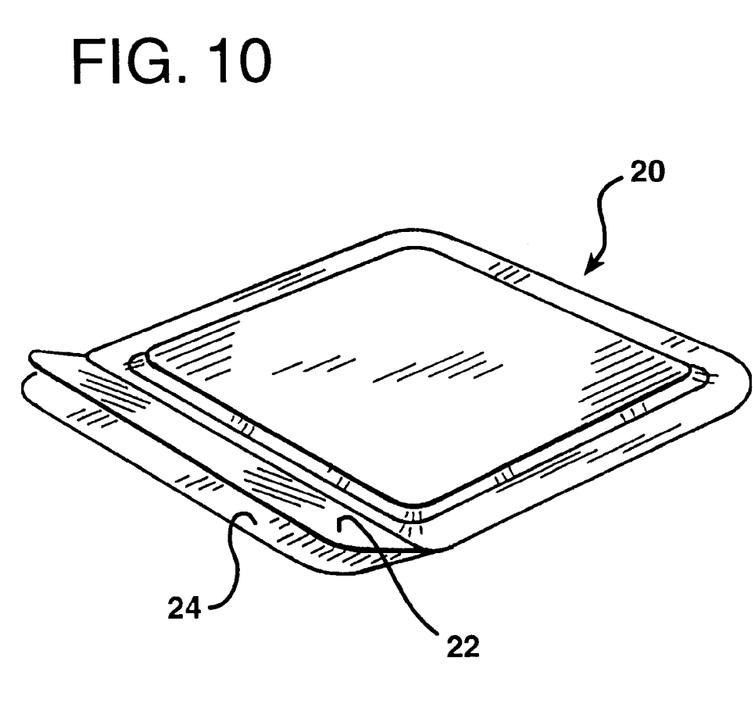
FIG. 10 is a perspective view of an alternative embodiment of the package with a free-lifting edge for peeling.

Another alternative embodiment of the invention is shown in FIG. 10, in which sheets 22 and 24 may be peeled apart and the entire wound packing removed. In this embodiment, one side portion of the perimeter of the package is sealed so that the edges of the two sheets are free-lifting and may be peeled apart. It will be appreciated that other variations of this embodiment may also be employed. For example, the package can be configured so that the sheets include a free-lifting corner section of the package. If desired, a tab may be included between the two sheets along an edge or in a corner to facilitate grasping and peeling apart of the sheets. The package may also include a cut or notch along an edge which will facilitate tearing for opening of the package.

Figures 5, 6:
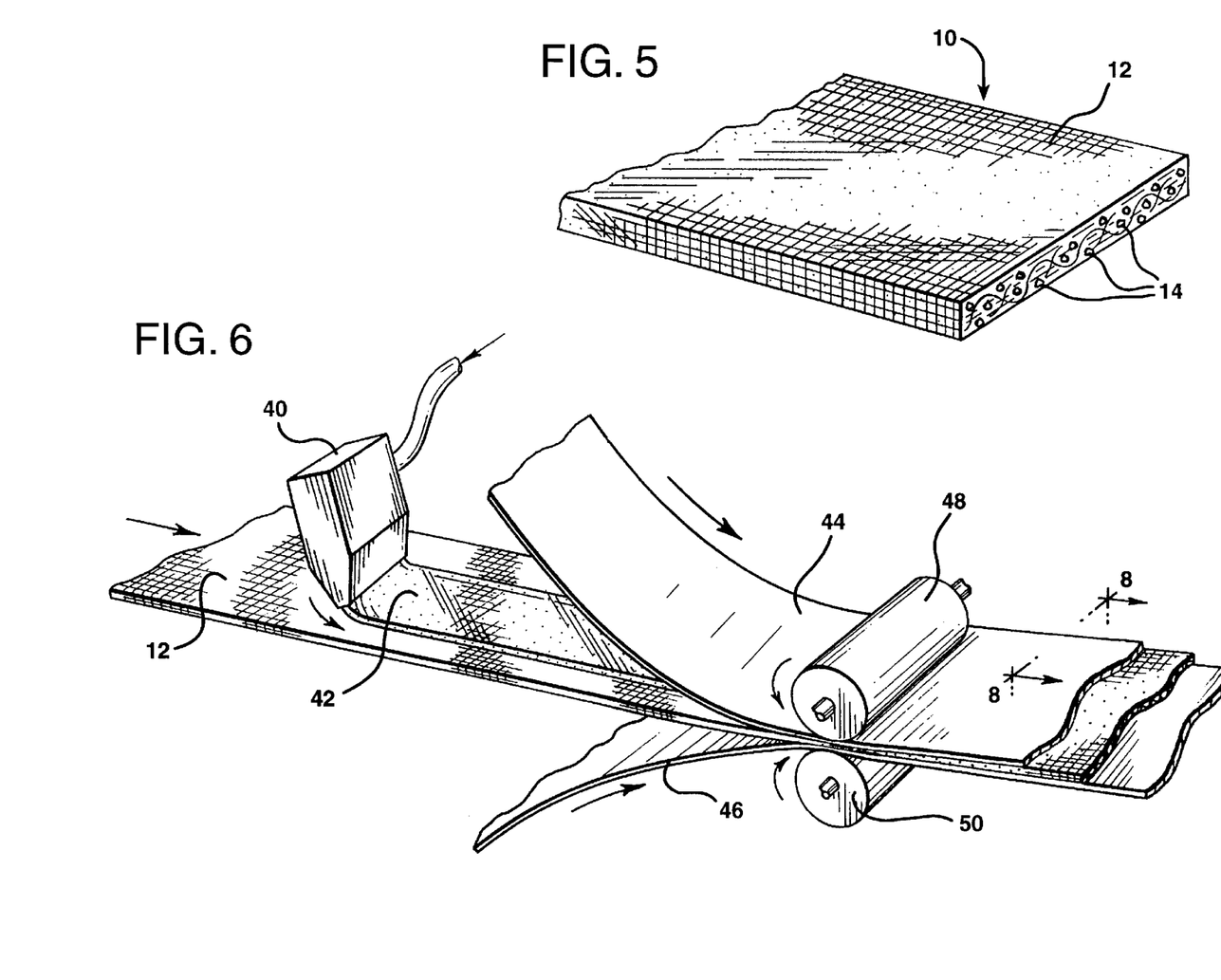
FIG. 5 is an enlarged, partially cut away perspective of one embodiment of the wound packing of the present invention.
FIG. 6 is a schematic view illustrating a process by which the wound packing of FIG. 5 can be made.

While it is within the scope of the invention for absorbent layer 12 to contain no coatings or impregnants (for example, sterile woven gauze is a useful wound packing material), it may be desirable to include in absorbent layer 12 a hydrogel material which may be hydrated or dehydrated. FIG. 5 illustrates (in a greatly enlarged view for purposes of illustration) one embodiment of the invention in which wound packing 10 (prior to being cut into its spiral configuration) comprises an absorbent layer 12 having dehydrated hydrogel material 14 impregnated therein for absorbing wound exudate. It is preferable that dehydrated hydrogel material 14 is completely impregnated in the interstices between fibers of the absorbent layer 12. It is also preferable to have dehydrated hydrogel material 14 completely impregnated in the interstices of absorbent layer 12 such that dehydrated hydrogel material 14 is substantially exposed at the outer surfaces of wound packing 10 so that absorbent layer 12 is precluded from adhering to the patient's wound. Further, dehydrated hydrogel material 14 must be able to adhere to the absorbent layer 12 so as to form a flexible, thin, structure which, when contacted with a draining wound on a patient, absorbs large amounts of wound exudate without inhibiting the healing of such wound. In this manner, wound packing 10 can be removed from the wound to which it is adhered in a non-destructive manner such that it does not adhere to the new cell tissue forming in the healing wound. Wound dressing 10 also does not break apart into fragments or lumps, but rather, can be removed substantially as a single piece because of its woven or intertwined fibrous composition. Such features have not been present in past thin, flexible, gauze-type wound dressings. These features are largely attributed to the hydrogel material from which dehydrated hydrogel material 14 is formed. These materials are discussed more fully below.

For purposes of providing a more intuitive understanding of the wound packing 10, a process by which the wound packing 10 can be made, is schematically illustrated in FIG. 6. As seen in FIG. 6, absorbent layer 12 is fed in continuous web form under an applicator 40 capable of receiving and applying a liquid or uncured hydrogel material 42 from a source (not shown) without permitting it to cure within its components. Applicator 40 applies uncured hydrogel material 42 onto absorbent layer 12 in an amount sufficient to impregnate the interstices therein and provide exposure of the hydrogel at the outer surfaces of layer 12. As those skilled in the art will appreciate, the amount of uncured hydrogel material 42 applied will vary with the particular material used as absorbent layer 12 and the width and thickness of the web to be coated. It is preferable for a pair of release sheets 44 and 46 to encompass the absorbent layer 12 so as to provide protection for subsequent processing.

A pair of rollers 48, 50 cooperate with one another to compress release sheets 44, 46 together such that the uncured hydrogel material 42 spreads evenly on and into absorbent layer 12. Preferably, release sheets 44, 46 are releasably secured to absorbent layer 12 such that they may be removed prior to use or packaging. Alternatively, one or both of the release sheets may be used as a stiffening means in package 20 (see FIG. 4). FIG. 6 illustrates wound packing 10 having the absorbent layer 12 impregnated with uncured hydrogel material 42 which is sandwiched between the release sheets 44, 46. Uncured hydrogel material 42 is then allowed to cure downstream to form a hydrated hydrogel material 52 surrounding and impregnating absorbent layer 12 (FIG. 8)

Thereafter, the continuous web of wound packing 10 may be cut into individual sheets, spiral cut to the form shown in FIG. 1, and then packaged. Cutting may be accomplished through the use of steel-rule dies or the like. The hydrogel may be in a hydrated or dehydrated condition. If it is desired to dehydrate the hydrogel, wound packing 10 is first dried, oven-baked or otherwise dehydrated so as to substantially completely evaporate the water contained in the hydrogel material 52 which was applied onto absorbent layer 12. Release sheets 44, 46 may be removed, or may remain with the wound packing as it is packaged. The result is a finished, flexible, and sterile wound packing 10 sealed in package 20.

Figure 7:
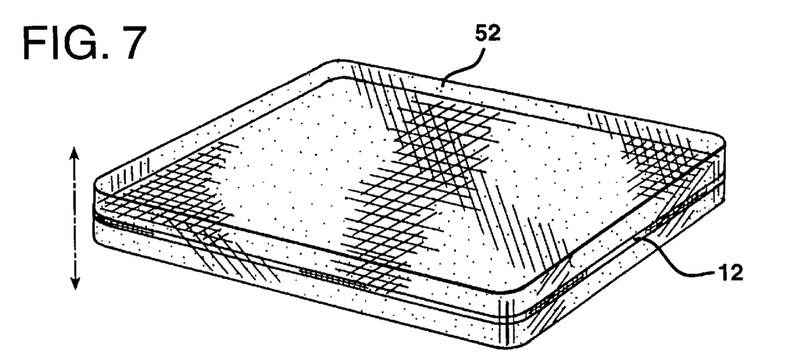
FIG. 7 illustrates one embodiment of the wound packing after it has been applied to a draining wound.

Referring now to FIG. 7, which has been greatly enlarged for purposes of illustration, a small piece of wound packing 10, after having been contacted with a draining wound, is illustrated. Where a dehydrated hydrogel has been used, FIG. 7 illustrates the expansion or swelling (as depicted by the arrows in dotted lines) of the dehydrated hydrogel material 14 upon acquisition of bodily fluids, such as wound exudate, from the wound to which the wound packing 10 is applied. The expanded or hydrated hydrogel material is referred to herein by reference numeral 52. Wound dressing 10, when it contains optional dehydrated hydrogel 14, is therefore analogous to a sponge in that its initial dehydrated state expands as fluids are absorbed.

Figure 8:
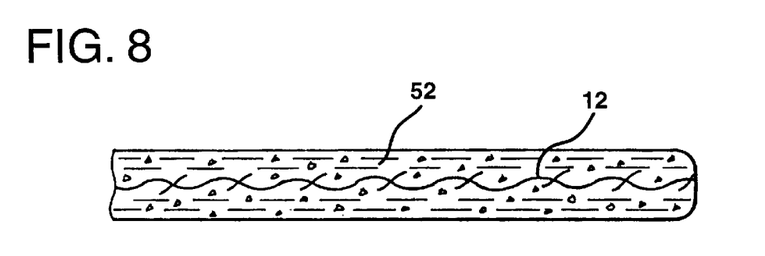
FIG. 8 is a cross-sectional view of the wound packing of FIGS. 6 and 7.

FIG. 8 may also be considered to illustrate a cross-sectional view of a small piece of wound dressing 10 depicted in FIG. 7 and shows hydrogel material 52 swelled in and around absorbent layer 12. As those skilled in the art will appreciate, hydrogel material 52 depicted in FIG. 7 is the same as the cured hydrogel material 52 discussed with respect to the process by which wound packing 10 is made and illustrated in FIG. 6. In essence, cured and hydrated hydrogel material 52 may be initially dehydrated for packaging and then returned to its original hydrated state upon wound exudate absorption.

The preferred hydrogel material for use in the present invention is formed from an aqueous mixture of polyhydric alcohol, an aliphatic diisocyanate terminated prepolymer, polyethylene oxide based diamine and sodium chloride. Preferably, the polyhydric alcohol is selected from the group consisting of polypropylene glycol, polyethylene glycol and glycerine. The hydrogel material 52 in its dehydrated state, which is referred to herein as the dehydrated hydrogel material 14, provides a highly absorbent material capable of retaining large amounts of wound exudate, thereby rendering it very suitable for use in wound packings. By forming the hydrogel material 52 from the aforementioned aqueous mixture, wound packing 10 remains intact as it absorbs wound exudate from the wound.

Moreover, the preferred hydrogel material does not adhere or stick to the wound thereby allowing for easy removal of wound packing 10 substantially as a single piece. Additionally, the biocompatibility of the hydrogel material within the wound is extremely favorable. Thus, the resulting hydrogel material 52, and therefore the dehydrated hydrogel material 14, provides a bio-compatible, non-irritating, fluid absorbing, bacterial protective, cushioning, skin-like media over the wound site. An additional advantage of the hydrogel material 52 is that it may be transparent, rendering it possible to inspect the wound site through absorbent layer 12 without removing wound packing 10 for those embodiments where 5 the openings between fibers in layers 12 are sufficient to permit viewing.

The preferred aliphatic diisocyanate terminated prepolymer is an isophorone diisocyanate terminated prepolymer based on polyols containing more than about 40% polyethylene oxide and having an isocyanate content of about 3% by weight. The molecular weight of the isophorone diisocyanate terminated prepolymer is preferably in a range from about 1500 to about 8000 and most preferably, from about 4000 to about 5000. The polyethylene oxide based polyamine is preferably a polyethylene oxide based diamine having a molecular weight in a range from about 200 to about 6000 and most preferably, about 2000. It is also preferable that the aliphatic diisocyanate terminated prepolymer and the polyethylene oxide based polyamine have a stoichiometric ratio of about 1:1. Those skilled in the art will appreciate that all of the constituents with the preferred hydrogel material may be readily synthesized or purchased commercially neither of which is more preferred.

It has been found that a more preferred hydrogel material 52, and therefore the dehydrated hydrogel material 14, is formed from an aqueous mixture including from about 0% to about 90% by weight polyhydric alcohol; from about 6% to about 60% by weight aliphatic diisocyanate terminated prepolymer; from about 4% to about 40% by weight polyethylene oxide based polyamine; up to about 2% by weight sodium chloride; and the balance water. A more preferred hydrogel composition for forming the hydrogel material 30 is formed from a mixture comprising from about 15% to about 30% by weight polypropylene glycol; from about 8% to about 14% by weight isophorone diisocyanate terminated prepolymer; from about 5% to about 10% by weight polyethylene oxide based diamine; and up to about 1% by weight sodium chloride; and the balance water. Most preferably, the hydrogel material 30 is formed from a mixture comprising: (a) from about 16% to 17% by weight polypropylene glycol; (b) from about 10% to 12% by weight isophorone diisocyanate terminated prepolymer; (c) from about 7% to 9% by weight polyethylene oxide based diamine; (d) about 0.5% to 1% by weight sodium chloride; and (e) the balance water.

The aforementioned preferred hydrogel compositions provide a wound packing 10 having the desired properties of excellent biocompatibility and absorption of exudate properties without adhering to the wound. However, other materials having such characteristics, including but not limited to the aforementioned hydrogel compositions, may be used to form the hydrogel material 52 in accordance with the present invention.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A wound packing comprising:
    a flexible wound packing material capable of absorbing wound exudate, said flexible material being in the form of a substantially flat, coiled, spirally-cut layer impregnated with a hydrogel material.

2. The wound packing of claim 1 in which said flexible material is selected from the group consisting of woven gauze, fabric, nonwoven natural or synthetic fibers, polymeric sheets and films.

3. A wound packing comprising:
    a flexible wound packing material capable of absorbing wound exudate, said flexible material being in the form of a substantially flat, coiled, spirally-cut layer impregnated with a hydrocolloid.

4. A wound packing comprising:
    a flexible wound packing material capable of absorbing wound exudate, said flexible material being in the form of a substantially flat, coiled, spirally-cut layer impregnated with a medicament.

5. The wound packing of claim 1 in which said hydrogel is a dehydrated hydrogel.

6. The wound packing of claim 5 in which said wound packing has outer surfaces and in which said hydrogel is substantially exposed at said outer surfaces of said wound packing.

* * * * *